US00PP27964P2

(12) United States Plant Patent
Hartman

(10) Patent No.: US PP27,964 P2
(45) Date of Patent: May 2, 2017

(54) ***CALADIUM* PLANT NAMED 'RFL 2317-114'**

(50) Latin Name: *Caladium×hortulanum*
Varietal Denomination: RFL 2317-114

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 14/998,535

(22) Filed: Jan. 16, 2016

(51) Int. Cl.
*A01H 5/02* (2006.01)

(52) U.S. Cl.
USPC ..... Plt./373

(58) Field of Classification Search
USPC ..... Plt./373
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'RFL 2317-114', characterized by its intermediate to tall height, upright and uniformly mounded plant habit; vigorous growth habit and very rapid growth rate; fancy type leaves that are dark green in color with red-colored venation, bright red-colored areas surrounding the veins and salmon pink-colored spots; and above average tolerance to *Xanthomonas* Leaf Spot.

4 Drawing Sheets

Botanical designation: *Caladium×hortulanum.*
Cultivar denomination: 'RFL 2317-114'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'RFL 2317-114'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium×hortulanum* 'Frieda Hemple', not patented, as the female, or seed, parent with *Caladium×hortulanum* 'Red Flash', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RFL 2317-114'. These characteristics in combination distinguish 'RFL 2317-114' as a new and distinct *Caladium* plant:

1. Intermediate to tall in height, upright and uniformly mounded plant habit.
2. Vigorous growth habit and very rapid growth rate.
3. Fancy type leaves that are dark green in color with red-colored venation, bright red-colored areas surrounding the veins and salmon pink-colored spots.
4. Above average tolerance to *Xanthomonas* Leaf Spot.

Plants of the new *Caladium* differ primarily from plants of the female parent, 'Frieda Hemple', in leaf color as leaves of 'Frieda Hemple' are medium green in color with bright red-colored centers and venation.

Plants of the new *Caladium* differ primarily from plants of the male parent, 'Red Flash', in the following characteristics:

1. Plants of the new *Caladium* are shorter than plants of 'Red Flash'.
2. Plants of the new *Caladium* are less apically dominant and are denser than plants of 'Red Flash'.
3. Plants of the new *Caladium* have a more rapid growth rate than plants of 'Red Flash'.
4. Plants of the new *Caladium* and 'Red Flash' differ in leaf color as leaves of 'Red Flash' have red-colored venation and interveinal areas with pink and white-colored spots and dark green-colored borders.

Plants of the new *Caladium* can be compared to plants of *Caladium×hortulanum* 'Postman Joyner', not patented. In side-by-side comparisons, plants of the new *Caladium* differ primarily from plants of 'Postman Joyner' in the following characteristics:

1. Plants of the new *Caladium* and 'Postman Joyner' differ in leaf color as leaves of 'Postman Joyner' are dark green in color with bright red-colored centers.
2. Plants of the new *Caladium* and 'Postman Joyner' differ in leaf petiole color as leaf petioles of 'Postman Joyner' are close to black in color.

Plants of the new *Caladium* can be compared to plants of *Caladium×hortulanum* 'Blaze', not patented. In side-by-side comparisons, plants of the new *Caladium* differ primarily from plants of 'Blaze' in the following characteristics:

1. Plants of the new *Caladium* are taller than plants of 'Blaze'.
2. Plants of the new *Caladium* and 'Blaze' differ in leaf color as leaves of 'Blaze' are dark green in color with burgundy red-colored venation and centers.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'RFL 2317-114' in a container and grown in a shadehouse (tuber not de-eyed).

The photograph at the top of the second sheet is a comparison view of typical potted plants of the female parent, 'Frieda Hemple' (right), 'RFL 2317-114' (center) and the male parent, 'Red Flash' (left).

The photograph at the bottom of the second sheet is a comparison view of typical potted plants of 'Postman Joyner' (left), 'RFL 2317-114' (center) and 'Blaze' (right).

The photograph at the top of the third sheet is a comparison view of typical plants of 'RFL 2317-114' grown in containers; the plant on the left has not had its tuber de-eyed and the plant on the right has had its tuber de-eyed prior to planting.

The photograph at the bottom of the third sheet is a side perspective view of typical plants of 'RFL 2317-114' grown in an open field.

The photograph at the top of the fourth sheet is a close-up view of typical freshly-harvested tubers and roots of 'RFL 2317-114'.

The photograph at the bottom of the fourth sheet is a close-up view of a typical inflorescence of 'RFL 2317-114'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were eight weeks old (vegetative plant photographs and description) and eleven weeks old (inflorescence photograph and description), and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'RFL 2317-114'.

Parentage:

*Female, or seed, parent.*—*Caladium×hortulanum* 'Frieda Hemple', not patented.

*Male, or pollen, parent.*—*Caladium×hortulanum* 'Red Flash', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and somewhat flattened; individual segments ovate to round. Height: About 4.8 cm. Diameter: About 6 cm to 7.7 cm. Segment height: About 3.2 cm. Segment diameter: About 3 cm to 3.5 cm. Axillary buds, height: About 5 mm. Texture: Thick, starchy. Color: Epidermis, freshly-harvested: Close to 159A; outer skin, close to 199A and N199A. Epidermis, dried: Close to 200D. Cortical tissue: Close to 2D. Axillary buds: Close to 36A to 36B. Root description: Thick, fleshy contractile roots; color, close to 155C. Rooting habit: Medium density.

Plant description:

*Plant type.*—Herbaceous perennial; suitable as a potted plant in containers 15-cm to 25-cm and suitable as a landscape plant in shaded areas.

*Plant and growth habit.*—Intermediate to tall in height, upright and uniformly mounded plant habit; vigorous and dense growth habit; very rapid growth rate; potted plants in finished or saleable form in about six to seven weeks after planting tubers; leaf petioles and leaves arise from one or more growing points on tubers; petioles mostly upright and outwardly leaning with development.

*Plant height, from soil level to top of foliar plane, shadehouse-grown potted plants.*—About 35 cm to 43 cm.

*Plant height, from soil level to top of inflorescences, shadehouse-grown potted plants.*—About 40.5 cm.

*Plant diameter or spread, shadehouse-grown potted plants.*—About 45 cm to 51 cm.

*Number of shoots per plant, shadehouse-grown potted plants, tubers not de-eyed.*—About three develop per #1 tuber.

*Number of shoots per plant, shadehouse-grown potted plants, tubers de-eyed.*—About three to four develop per #1 tuber.

*Cataphylls, shadehouse-grown potted plants.*—Length: About 6 cm to 8.8 cm. Width: About 1.5 cm to 1.8 cm. Shape: Wedge-shaped. Apex: Acute. Base: Sheathing the stem. Color, inner surface: Close to 196D; colors and patterns on the outer surface are visible on the inner surface. Color, outer surface: Close to N170D tinged with close to 69D, stippled, streaked and tessellated with close to 147A tinged with close to 200A; with development, color becoming closer to 199A stained with close to 187B.

Leaf description:

*Arrangement and type*.—Alternate; simple; fancy-type.

*Length, shadehouse-grown potted plants*.—About 21 cm to 28 cm.

*Width, shadehouse-grown potted plants*.—About 14 cm to 21 cm.

*Shape*.—Ovate, cordate.

*Apex*.—Cuspidate.

*Base*.—Sagittate to peltate.

*Margin*.—Entire; mostly flat with broad undulations.

*Texture, upper and lower surfaces*.—Smooth, glabrous.

*Luster, upper surface*.—Slightly glossy to dull sheen.

*Luster, lower surface*.—Glaucous, dull sheen.

*Venation pattern*.—Pinnate.

*Color, shadehouse-grown potted plants*.—Developing leaves, upper surface: Midvein and primary veins: Close to 53B tinged with close to 53A. Secondary veins: Close to 183A tinged with close to 53B. Areas surrounding venation: Close to 53B. Interveinal areas: Close to 183A tinged with close to 53B; spots, close to 51B. Margins: Towards the margins, close to 147A and 139A; thin margin, close to 187A. Basal notch: Close to 187A. Developing leaves, lower surface: Midvein and primary veins: Close to 184B. Secondary veins: Close to 183C. Areas surrounding venation: Close to 184A. Interveinal areas: Close to 191A; spots, close to 182D. Margins: Thin margin, close to 187A. Basal notch: Close to 187A. Fully expanded leaves, upper surface: Midvein and primary veins: Close to 53A. Secondary veins: Close to 183A tinged with close to 53A. Areas surrounding venation: Close to 53B tinged with close to 53A. Interveinal areas: Close to 183A tinged with close to 53A and close to 147A tinged with close to 189A; spots, close to 51C. Margins: Towards the margins, close to 147A tinged with close to 189A; thin margin, close to 187A. Basal notch: Close to 187A. Fully expanded leaves, lower surface: Midvein: Close to 185B to 185C. Primary veins: Close to 182D. Areas surrounding venation: Close to 184A. Interveinal areas: Close to lighter than 187B and close to 191A tinged with close to 189A; spots, close to 182D. Margins: Thin margin, close to 187A. Basal notch: Close to 187A.

*Petioles*.—Aspect: Initially upright and straight; with development, leaning outwardly; flexible. Length, shadehouse-grown potted plants: About 22 cm to 31.5 cm. Diameter, distally, shadehouse-grown potted plants: About 3 mm to 5 mm. Diameter, proximally, shadehouse-grown potted plants: About 7 mm to 10 mm. Texture: Smooth, glabrous; glaucous. Color, shadehouse-grown potted plants: Close to 181C to 181D densely streaked, stippled and tessellated with close to 200A tinged with close to 147A; below the leaf and petiole junction, close to 181A and 181C typically tinged with close to 53B. Wing length, shadehouse-grown potted plants: About 5 cm to 8.8 cm. Wing diameter, shadehouse-grown potted plants: About 8 mm to 12 mm. Texture, inner and outer surfaces: Smooth, glabrous. Luster, inner and outer surfaces: Dull to slightly glossy. Wing color, shadehouse-grown potted plants: Inner surface: Close to 196D; colors and patterns on the outer surface are visible on the inner surface. Outer surface: Close to N170D and 69D, streaked, stippled and tessellated with close to 147A tinged with close to 200A.

Inflorescence description: Inflorescences observed on eleven week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; light sweet, jasmine-like with camphor note.

*Natural flowering season and flower longevity*.—Plants of the new *Caladium* typically flower during the spring and summer in central Florida; flowers develop about eleven weeks after growth commences; inflorescences last about three days before fading; inflorescences persistent.

*Spathe*.—Length, overall: About 12.2 cm. Length, distal open portion: About 8 cm. Length, proximal closed portion: About 4.2 cm. Width, distal open portion: About 3.8 cm. Depth, distal open portion: About 3.2 cm. Width, at constriction: About 1.5 cm. Width, proximal closed portion: About 3.2 cm. Shape: Elliptic to slightly obovate. Apex: Acuminate. Base: Obtuse. Margin: Entire. Texture, front and rear surfaces: Smooth, glabrous. Luster, front surface: Dull sheen. Luster, rear surface: Glaucous, dull sheen. Color, front surface: Distal open portion: Close to 155C; margins tinged with close to 157B; with development, color becoming closer to 199D. Proximal closed portion: Proximally, close to 194C, 194B and 147C; proximally flushed, streaked and mottled with close to 187A and 187B; margins, tinged with close to 182D; color does not change with development. Color, rear surface: Distal open portion: Close to 155B, 155C and areas close to 145D; color does not change with development. Proximal closed portion: Variably streaked and mottled with close to 147C, 146B and 146C; margins, faintly tinged with close to 182D; color does not change with development.

*Spadix*.—Length, overall: About 9.6 cm. Length, male flower zone: About 5.6 cm. Length, sterile zone: About 1.9 cm. Length, female flower zone: About 2.1 cm. Diameter, male flower zone: About 1.1 cm. Diameter, sterile flower zone: About 8 mm. Diameter, female flower zone: About 1.1 cm. Shape: Columnar, spindle-shaped. Apex: Acute to bluntly acute. Base: Obtuse. Aspect: Upright. Color, mature, male zone: Close to 158D. Color, mature, sterile zone: Close to 155D. Color, mature, female zone: Close to 155B and 11D. Male flowers: Quantity per spadix: About 308. Shape: Obovate. Height: About 3.5 mm. Diameter: About 3.5 mm. Pollen amount:

Abundant. Pollen color: Close to 8D. Female flowers: Quantity per spadix: About 280. Shape: Obovate. Height: About 2.5 mm. Diameter: About 2 mm. Stigma color: Close to 155B. Ovary color: Close to 11D.

*Scape*.—Length: About 30.9 cm. Diameter: About 7 mm. Strength: Sturdy; flexible. Aspect: Mostly erect. Texture: Smooth, glabrous. Luster: Dull to slightly glossy; glaucous. Color: Close to 199D and close to 199D tinged with close to 147D; streaked and stippled with close to 200A and 200B and variably tinged with close to 182D; just below spathe, close to 147C to 147D.

*Seeds and fruits*.—To date, seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'RFL 2317-114' as illustrated and described.

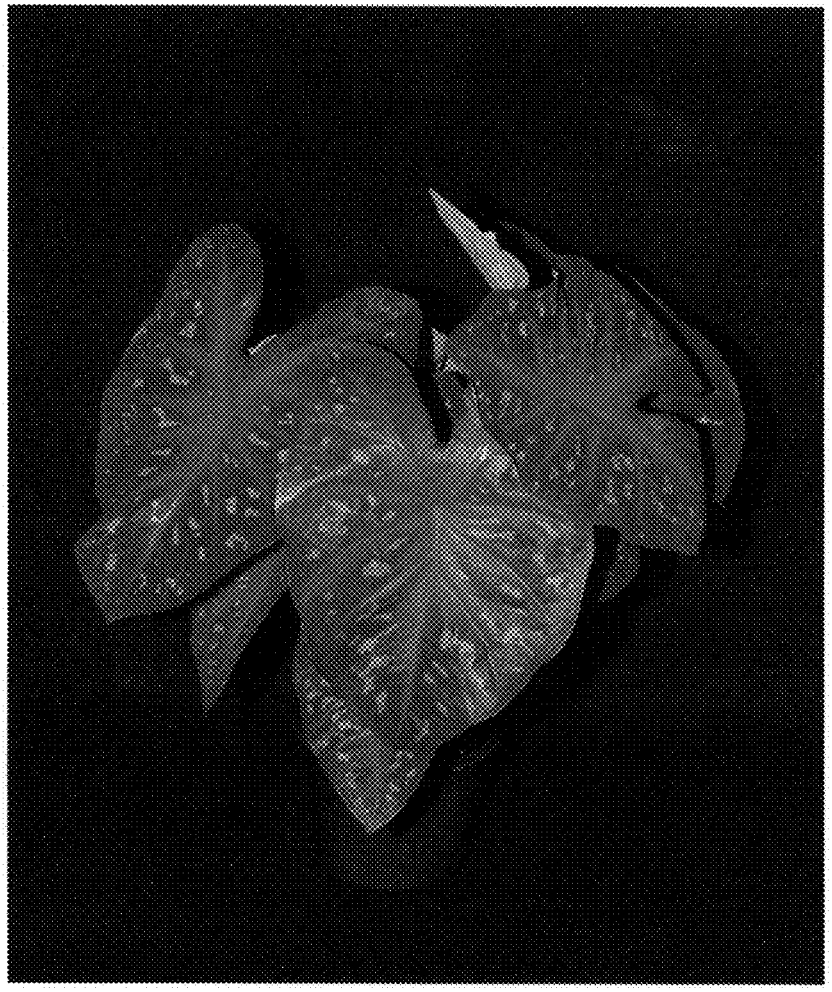

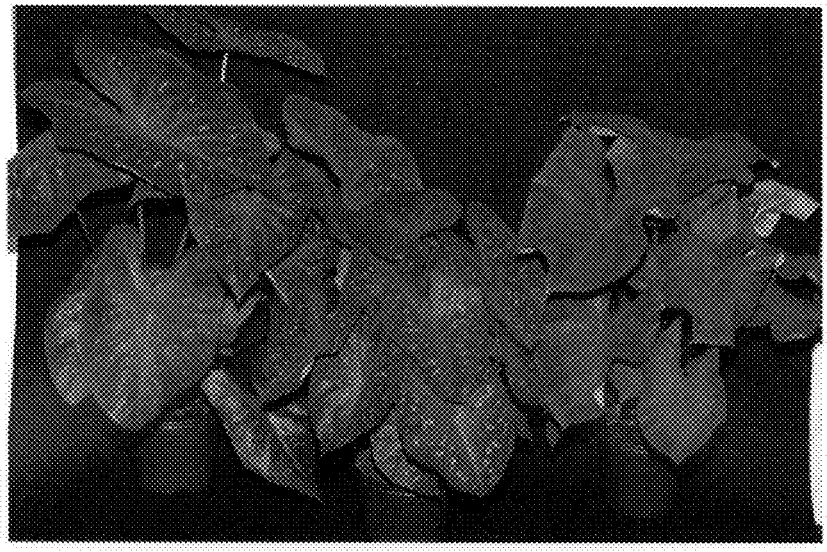
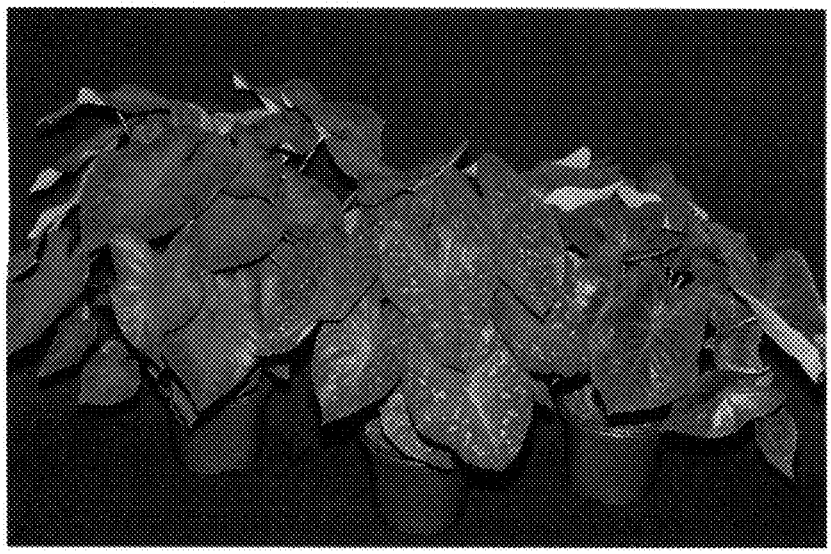

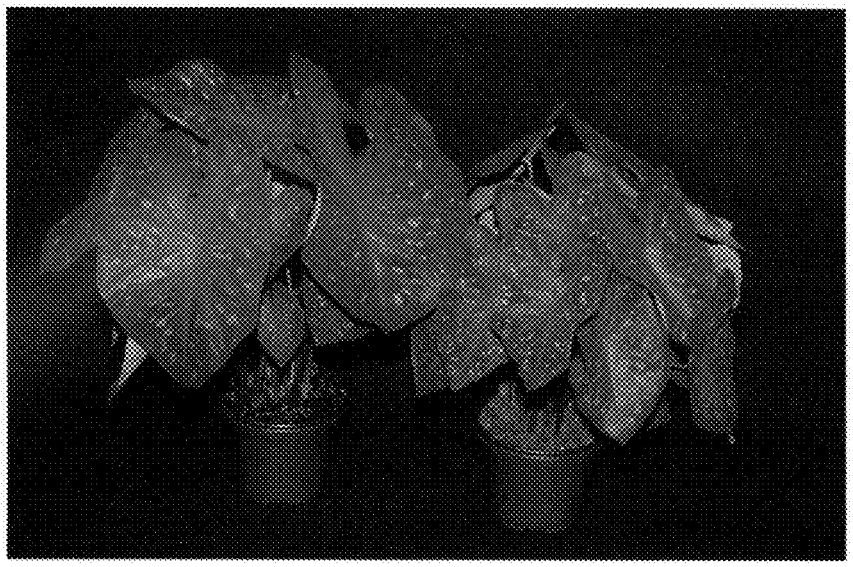
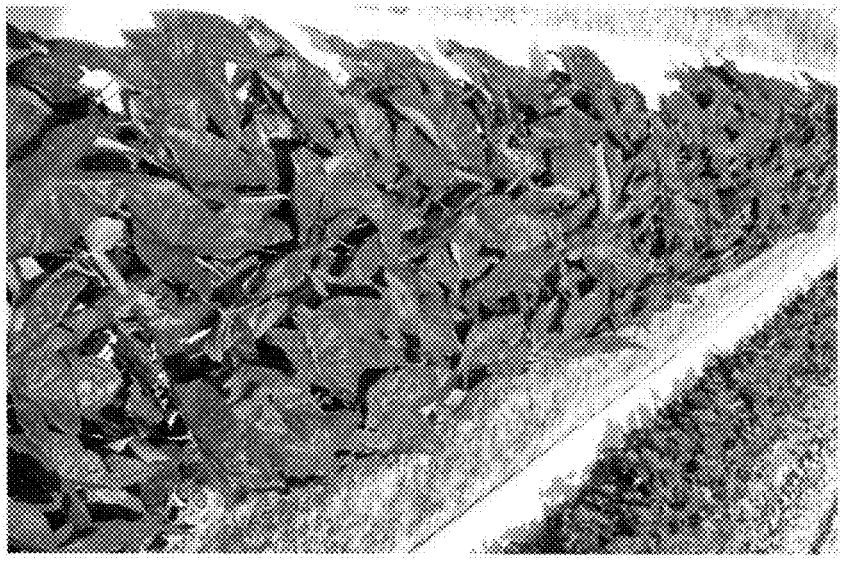

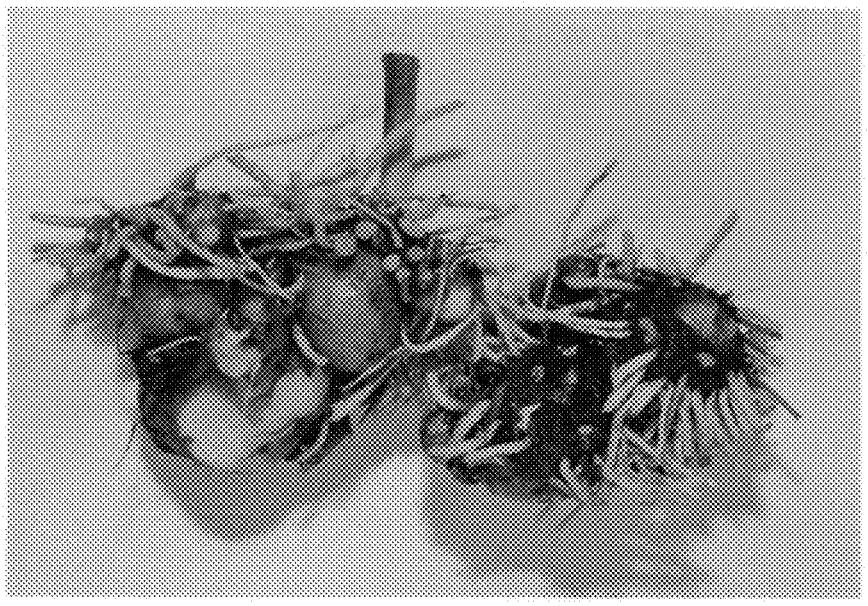
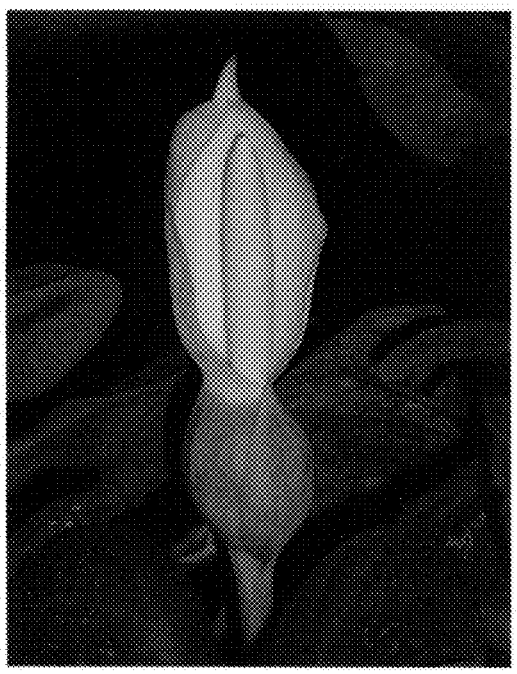

* * * * *